United States Patent [19]

Bonds

[11] Patent Number: Plant 7,068

[45] Date of Patent: Dec. 12, 1989

[54] ALMOND TREE, "LODI"

[76] Inventor: Irwin H. Bonds, P.O. Box 1698, Twain Harte, Calif. 95383

[21] Appl. No.: 280,226

[22] Filed: Dec. 5, 1988

[51] Int. Cl.[4] ..... A01H 5/00
[52] U.S. Cl. ..... Plt./30
[58] Field of Search ..... Plt. 30

*Primary Examiner*—Robert E. Bagwill

*Attorney, Agent, or Firm*—Worrel & Worrel

[57] ABSTRACT

A new and distinct variety of Almond Tree which is somewhat remotely similar to the Nonpareil Almond Tree (unpatented) but from which it is distinguished therefrom by producing a crop which is mature for commercial harvesting and shipment approximately Sept. 1 under the ecological conditions prevailing in Hickman, Calif.

1 Drawing Sheet

The present invention relates to a new and distinct variety of almond tree which has been denominated varietally as "Lodi" and more particularly to such an almond tree which blooms at approximately the same time of the season as the Nonpareil, a well known unpatented almond cultivar, and which is mature for commercial harvesting and shipment approximately five to seven days after the Nonpareil variety. The subject variety further is distinguished as to novelty by producing a plump kernel which has an aromatic characteristic and a pleasing somewhat slightly bitter almond flavor.

It has long been known that the marketability of almonds may be influenced to some degree by the "blendability" of the almond with the current "California" marketing classification. The "Lodi" almond tree appears to produce such a crop. It has been recognized that it is desirable to provide an almond tree bearing a crop which is ripe for commercial harvesting and shipment in late August and which has the commercially aesthetic appeal such as that presented by the "Lodi" almond tree. The nut of the subject variety is noteworthy in that it displays a propensity for producing a soft well sealed shell and a kernel with a noteworthy flavor and aroma.

ORIGIN AND ASEXUAL REPRODUCTION OF THE NEW VARIETY

The present variety of almond tree was discovered as a chance seedling of unknown parentage growing within the cultivated area of a public right of way in the Manteca area of the central San Joaquin Valley. More particularly the seedling was discovered by the inventor along Austin Road, in the cultivated area of the public right of way during routine orchard operations in 1976. The inventor noted the novel characteristics of the instant variety and marked the chance seedling for subsequent observation.

The first asexual reproduction of the present variety of almond tree occurred in 1977 when the inventor removed buds from the chance seedling and budded them into test trees which were then growing on the David Wilson Nursery growing grounds on Lake Road in Hickman, Calif. The test trees have been continually observed by the inventor and it has subsequently been determined that the budded test trees produced progeny which have identical characteristics to that observed in the original chance seedling.

SUMMARY OF THE NEW VARIETY

The "Lodi" Almond Tree is characterized principally as to novelty by producing a consistently good quality, early season nut. The present variety of almond tree bears a heavy, regular and well distributed crop which is mature for commercial harvesting and shipment approximately with the Price Almond Tree (believed unpatented) and 5–7 days after the Nonpareil almond tree (unpatented). As compared to the Nonpareil almond tree, the "Lodi" almond tree produces a crop which has a distinctive, pleasing, very slighly bitter almond flavor which is more pronounced and aromatic than the sweet almond flavor of the Nonpareil almond tree. Further, the claimed variety has a better shell seal than the crop produced by the Nonpareil almond tree and yields more consistently from year to year. Moreover the present variety of almond tree is compatible with Marianna 2624 rootstock and the kernel is currently considered blendable with the "California" marketing classification.

BRIEF DESCRIPTION OF THE DRAWINGS

The accompanying drawing is an illustration by photographic reproduction of a portion of a branch of an almond tree of the new variety showing a mature crop arranged in clusters along the branch. Further, the drawing also illustrates mature whole nuts, both with and without the shells removed, which are representative of the crop borne by the new variety of Almond Tree, denominated varietally as "Lodi".

DETAILED DESCRIPTION

Referring more particularly to the specific botanical details of this new and distinct variety of almond tree, the following has been observed under the ecological conditions prevailing at the applicant's employer's orchard which is located at 19701 Lake Road, Hickman, Calif. The Inter-Society Color Council, National Bureau of Standards, is utilized as the source of all major color code designations. Common color names are also used occasionally.

Generally:

*Size.*—Medium and upright, depending upon pruning practices.

*Vigor.*—Average.

*Density.*—Considered open.

Trunk:

*Form.*—Generally — medium as compared with other common almond cultivars.
*Surface texture.*—Medium.

Branches:
*Form.*—Average as compared with otehr common almond cultivars.
*Surface texture.*—Smooth.
*Lenticels — Size.*—Medium.
*Lenticels — numbers.*—Numerous.
*Branching habit.*—Average.
*Color — new wood.*—Green (120. m. Y G). Occasionally some red coloration may appear on exposed surfaces (13 d. Red, - 16. d. Red).
*Color — mature wood.*—Brown (61. gy. Br).

Rootstock compatability: The subject variety is compatible with Marianna 2624 rootstock. This is in contrast to the Nonpareil variety of almond tree which is not compatible with same.

LEAVES

Foliage:
*Quantity.*—Abundant.

Size:
*Generally.*—Medium.
*Average length.*—Approximately 8.26 cm.
*Average width.*—Approximately 2.86 cm.

Shape:
*Generally.*—Lenceolate in form and having an oblique base and an acuminate tip.

Thickness: Thin.
Texture: Glabrous, although wrinkled.
Marginal form: Finely serrate, and pinnately net veined.

Petiole:
*Average length.*—Approximately 1.40 cm.
*Average thickness.*—Approximately 0.60 cm.

Petiole color: Green (120. m. Y G.).

Leaf color:
*Upwardly disposed surfaces.*—Green (125. m. 01 G).
*Downwardly disposed surfaces.*—Dull green, (120. m. Y G).

Leaf glands:
*Size.*—Medium.
*Form.*—Considered mixed.
*Average numbers.*—Generally three.
*Color.*—Green (120. m. Y G).

FLOWERS

Date of full bloom: Full bloom was achieved on March 1 at Hickman, Calif.
Bloom amount: Considered heavy for the particular species.
Bloom color: Pink (5. m. Pink).

CROP

Bearing: Considered regular.
Harvest period: September 1; the date of harvesting is considered early as compared with other common varieties, for example the date of harvesting is approximately with the Price Cluster Almond Tree (U.S. Plant Pat. No. 2,350) and 5-7 days after the Nonpareil Almond Tree (unpatented).
Productivity: Very heavy.
Distribution of nuts on tree: Well distributed throughout; the nuts appear on short spurs.
Tenacity: Hangs well on the tree. Further the variety is easy to harvest, and easy to hull.

HULL

Surface texture:
*Outer surface.*—Smooth.

Pits: Pitted.
Form: Regular.
Thickness:
*Generally.*—Thin, approximately 0.250 cm.

Flesh:
Texture.—Tough.

Suture:
Shape.—Flat and depressed.

Color at harvest time: Light green, (120. m. y G) and having no silvery sheen.
Dehiscence: The variety opens freely.
Splitting tendency: The variety splits along the suture.

NUT

Size:
*Generally.*—Medium to large.
*Average length.*—Approximately 3.49 cm.
*Average width.*—Approximately 22.23 mm.
*Average thickness.*—Approximately 15.88 mm.

Nuts Per Ounce: 25-30.
Form: Uniform.
Shape:
*Generally.*—Ovate.

Thickness: Medium.
Shell:
*Surface texture.*—Soft.

Outer shell: Crumbling.
Inner shell: Well sealed.
Color: Medium brown (76 ly Br).
Pits — size: Small, shallow, and irregular.
Pits — numbers: Few.
Base: Square.
Stem scar:
*Size.*—Small.

Apex:
*Shape.*—Sharp.

Wing:
*Shape.*—Narrow.

Inner surface:
*Color.*—Average.

Ventral streak:
*Color.*—Light.

Percent of kernel to nut: Approximately 61.6%.

KERNEL

Size:
*Generally.*—Medium to large.
*Average length.*—Approximately 2.54 cm.
*Average width.*—Approximately 15.88 mm.
*Average thickness.*—Approximately 7.94 mm.

Form: Ovate.
Thickness: Average.
Base:
*Shape.*—Square.

Stem scar:
*Size.*—Medium.

Apex:
*Shape.*—Acuminate, and sharp.

Plumpness: Considered smooth.
Pellicle:
*Thickness.*—Thin.

Pubescence: Medium.
Color: Light brown (57. l.Br).

Number of doubles produced: Few, generally less than 2%.

Defective kernels: Few, generally less than 1%

Flavor: Noteworthy, slightly bitter.

Quality: Good.

Although this new variety of almond tree possesses the described characteristics noted above as a result of the growing conditions prevailing in Stanislaus County, Calif., in the Central part of the San Joaquin Valley, it is to be understood that variations of the usual magnitude and characteristics incident to the changes in growing conditions, fertilization, pruning and pest control are to be expected.

Having thus described and illustrated my new variety of almond tree, what I claim as new and desire to secure by Plant Letters Patent is:

1. A new and distinct variety of almond tree, substantially as illustrated and described which is somewhat similar to the Nonpareil Almond Tree (unpatented), but from which it is distinguished therefrom and characterized principally as to novelty by its compatibility with Marianna 2624 rootstock and which further yields a very heavy crop from season to season, the variety producing a crop which consists of a distinctively flavored kernel having a pronounced, aromatic, very slightly bitter almond flavor, the variety ripe for harvesting and ahipment approximately September 1 under the ecological conditions prevailing in Hickman, Calif.

* * * * *

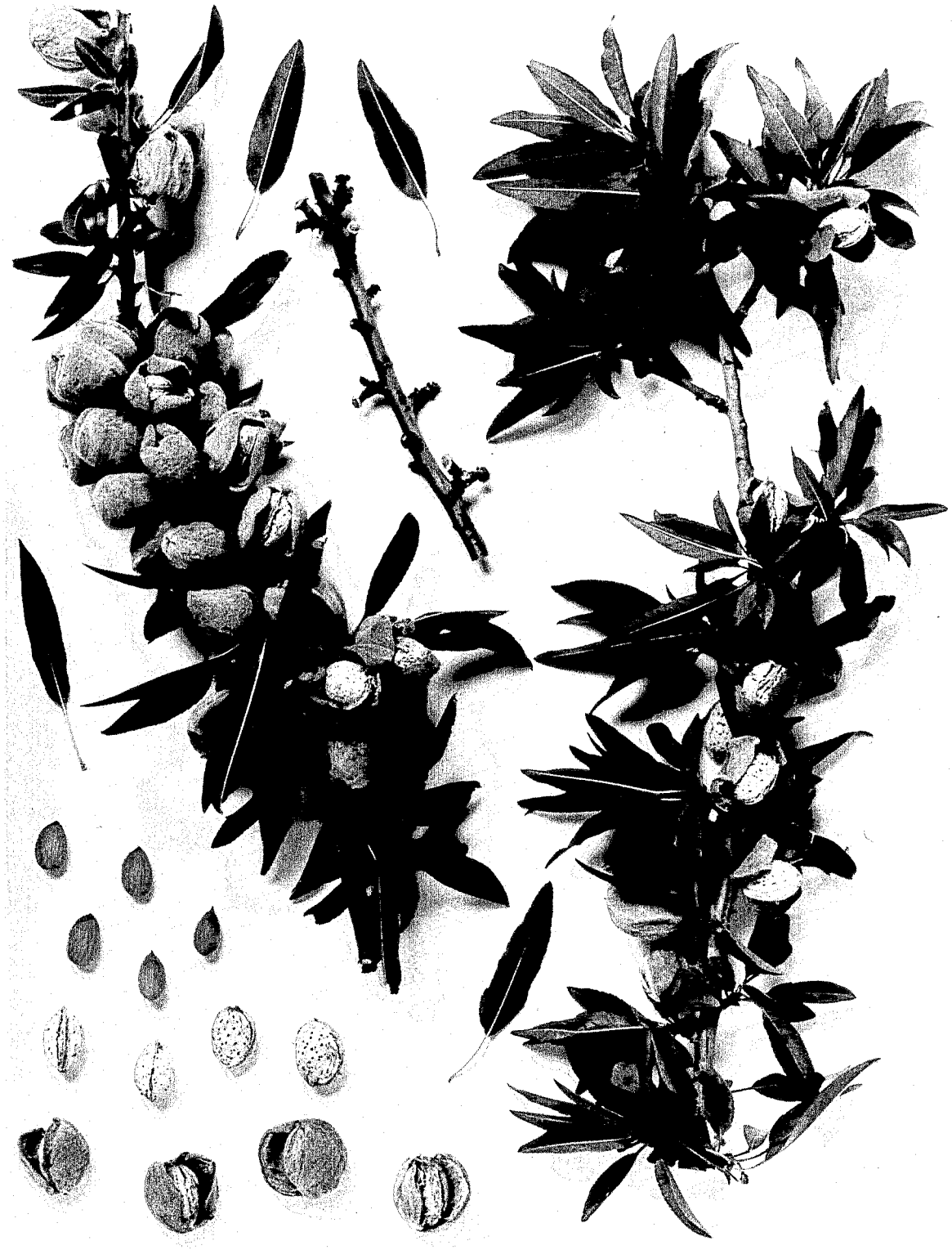

UNITED STATES PATENT AND TRADEMARK OFFICE

CERTIFICATE OF CORRECTION

PATENT NO. : PP. 7,068

DATED : December 12, 1989

INVENTOR(S) : Irwin H. Bonds

It is certified that error appears in the above-identified patent and that said Letters Patent is hereby corrected as shown below:

Column 2, line 44

Preceding "Generally", Insert ---TREE---

Column 3, Line 49

Between "bloom" and ":", Insert

---in 1984---

Signed and Sealed this

Eighth Day of January, 1991

*Attest:*

*Attesting Officer*

HARRY F. MANBECK, JR.

*Commissioner of Patents and Trademarks*